United States Patent [19]
Esch

[11] Patent Number: 5,946,441
[45] Date of Patent: Aug. 31, 1999

[54] LIGHT-DIFFUSING DEVICE FOR AN OPTICAL FIBER, METHODS OF PRODUCING AND USING SAME, AND APPARATUS FOR DIFFUSING LIGHT FROM AN OPTICAL FIBER

[75] Inventor: Victor C. Esch, Sunnyvale, Calif.

[73] Assignee: Indigo Medical, Inc., Palo Alto, Calif.

[21] Appl. No.: 08/819,687

[22] Filed: Mar. 17, 1997

Related U.S. Application Data

[63] Continuation of application No. 08/550,846, Oct. 31, 1995, abandoned.

[51] Int. Cl.$^6$ ........................................................ G02B 6/16
[52] U.S. Cl. ............................. 385/139; 385/31; 385/902; 606/16
[58] Field of Search ................................. 385/31, 36, 38, 385/115, 117, 134, 139, 902; 606/2, 15–17; 607/93

[56] References Cited

U.S. PATENT DOCUMENTS

| | | | |
|---|---|---|---|
| 4,233,493 | 11/1980 | Nath | 219/354 |
| 4,248,214 | 2/1981 | Hannah et al. | 604/93 |
| 4,336,809 | 6/1982 | Clark | 128/665 |
| 4,420,796 | 12/1983 | Nath | 219/354 |
| 4,448,547 | 5/1984 | Wickersheim | 374/131 |
| 4,652,143 | 3/1987 | Wickersheim et al. | 374/161 |
| 4,660,925 | 4/1987 | McCaughan | 128/665 |
| 4,676,231 | 6/1987 | Hisazumi et al. | 128/6 |
| 4,693,244 | 9/1987 | Daikuzono | 128/303.1 |
| 4,718,417 | 1/1988 | Kittrell et al. | 606/7 |
| 4,785,824 | 11/1988 | Wickersheim et al. | 128/736 |
| 4,822,123 | 4/1989 | Mori | 350/96.1 |
| 4,852,567 | 8/1989 | Sinofsky | 128/303.1 |
| 4,860,743 | 8/1989 | Abela | 606/7 |
| 4,878,492 | 11/1989 | Sinofsky et al. | 606/7 |
| 4,950,267 | 8/1990 | Ishihara et al. | 606/12 |
| 4,986,628 | 1/1991 | Lozhenko et al. | 350/96.29 |
| 5,042,980 | 8/1991 | Baker et al. | 606/7 |
| 5,074,632 | 12/1991 | Potter | 385/31 |
| 5,093,877 | 3/1992 | Aita et al. | 385/34 |
| 5,107,445 | 4/1992 | Jensen et al. | 364/525 |
| 5,119,461 | 6/1992 | Beyer et al. | 385/147 |
| 5,139,495 | 8/1992 | Daikuzono | 606/17 |
| 5,151,096 | 9/1992 | Khoury | 606/15 |
| 5,196,005 | 3/1993 | Doiron et al. | 606/7 |
| 5,207,669 | 5/1993 | Baker et al. | 606/7 |

(List continued on next page.)

FOREIGN PATENT DOCUMENTS

| | | |
|---|---|---|
| 0394446 | 10/1988 | European Pat. Off. . |
| 0391558 | 3/1990 | European Pat. Off. . |
| 0433464 | 3/1990 | European Pat. Off. . |
| 0377549 | 7/1990 | European Pat. Off. . |
| 0561903 | 11/1991 | European Pat. Off. . |
| 0622051 | 11/1993 | European Pat. Off. . |
| 0676218 | 10/1995 | European Pat. Off. . |
| 3119322 | 5/1981 | Germany . |
| 3119322 | 1/1983 | Germany . |
| 2953528 | 4/1983 | Germany . |
| 5-11852 | 2/1987 | Japan . |
| 2154761 | 9/1995 | United Kingdom . |
| WO8400800 | 3/1984 | WIPO . |
| 9002353 | 3/1990 | WIPO . |
| 9321840 | 11/1993 | WIPO . |
| 9325155 | 12/1993 | WIPO . |
| 9607451 | 3/1996 | WIPO . |

*Primary Examiner*—John D. Lee

[57] ABSTRACT

A diffusing tip is provided for diffusing light from a light-emitting end of an optical fiber in a radial distribution pattern relative to the axis of the tip and along a length of the tip. The tip has an inner core and an outer covering which define a light guide. The outer covering is modified on its interior surface adjacent to the core such that light transmitted down the light guide is removed from the core upon encountering a surface modification on the interior surface. The light so removed is transmitted to the outer surface along the length of the tip, where it can be used to irradiate a selected object or material. The diffusing tip preferably provides light in a substantially uniform intensity distribution for the substantially uniform irradiation of a selected object or material.

67 Claims, 3 Drawing Sheets

U.S. PATENT DOCUMENTS

| | | | |
|---|---|---|---|
| 5,209,748 | 5/1993 | Daikuzono | 606/16 |
| 5,269,777 | 12/1993 | Doiron et al. | 606/7 |
| 5,292,320 | 3/1994 | Brown et al. | 606/15 |
| 5,303,324 | 4/1994 | Lundahl | 385/147 |
| 5,312,392 | 5/1994 | Hofstetter et al. | 606/2 |
| 5,330,465 | 7/1994 | Doiron et al. | 606/15 X |
| 5,336,889 | 8/1994 | Hofstetter | 250/361 R |
| 5,337,381 | 8/1994 | Biswas et al. | 385/36 |
| 5,344,419 | 9/1994 | Spears | 606/15 |
| 5,363,458 | 11/1994 | Pan et al. | 385/31 |
| 5,363,463 | 11/1994 | Kleinerman | 385/123 |
| 5,373,571 | 12/1994 | Reid et al. | 385/31 |
| 5,380,318 | 1/1995 | Daikuzono | 606/16 |
| 5,401,270 | 3/1995 | Müller et al. | 606/13 |
| 5,429,635 | 7/1995 | Purcell, Jr. et al. | 606/17 |
| 5,431,647 | 7/1995 | Purcell, Jr. et al. | 606/16 |
| 5,496,308 | 3/1996 | Brown et al. | 606/15 |
| 5,536,265 | 7/1996 | van den Bergh et al. | 606/2 |

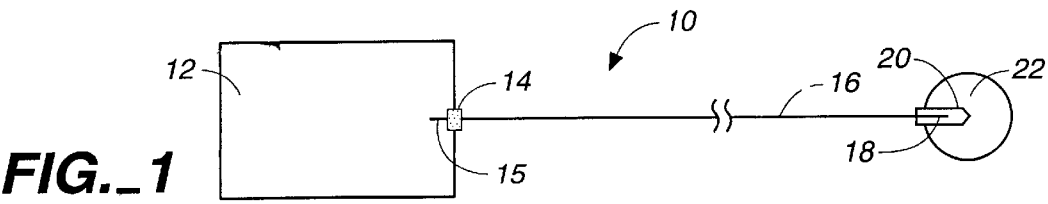
FIG._1
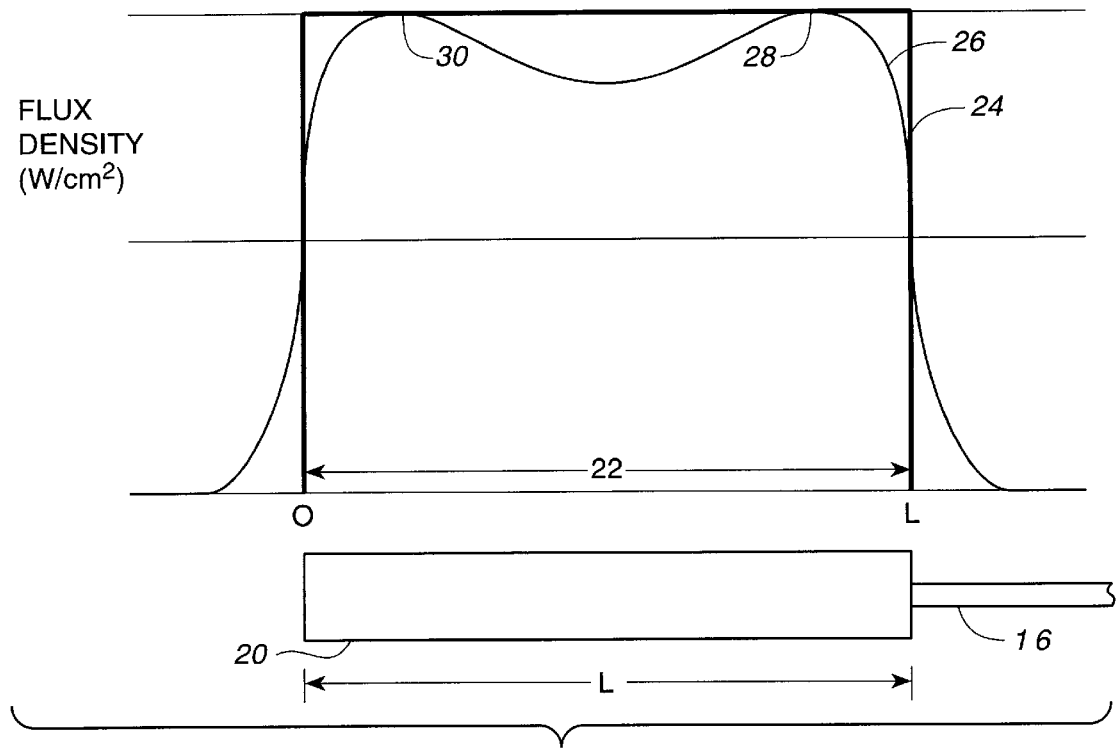
FIG._2
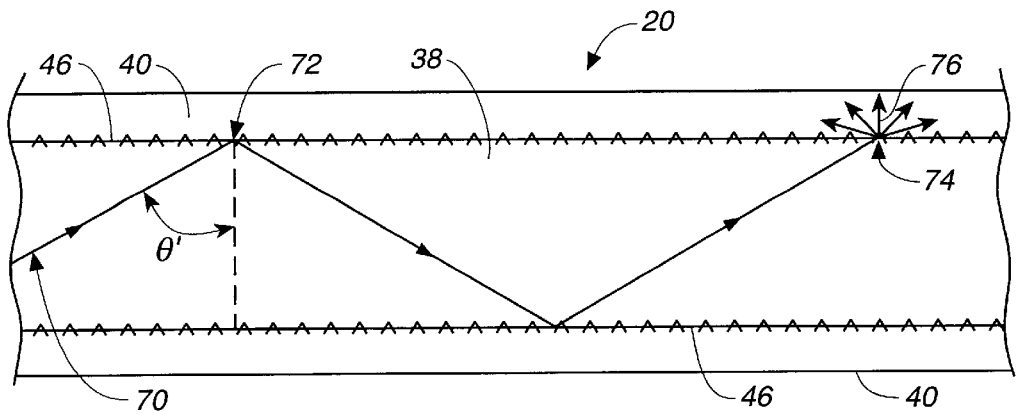
FIG._10

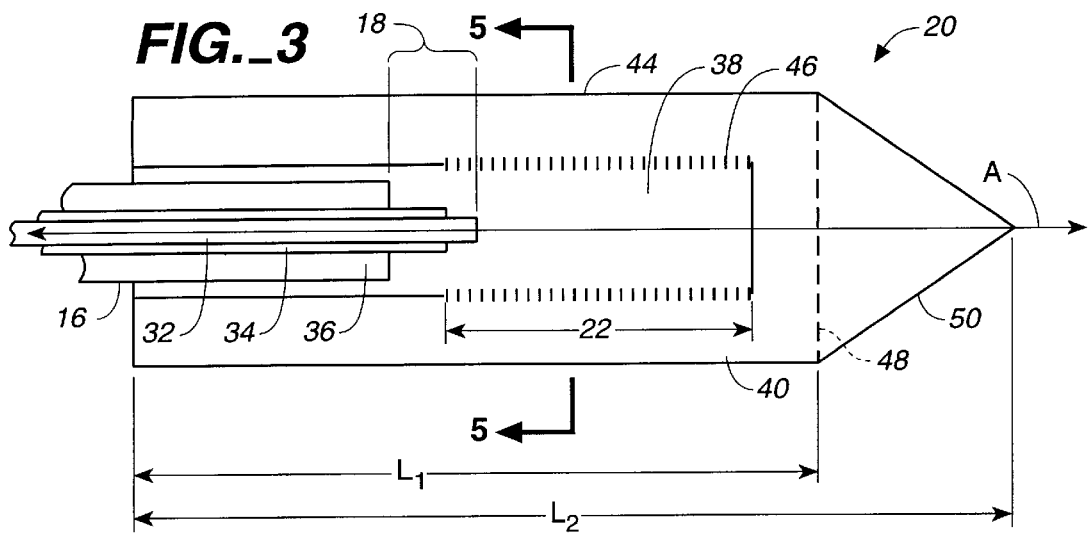
FIG._3
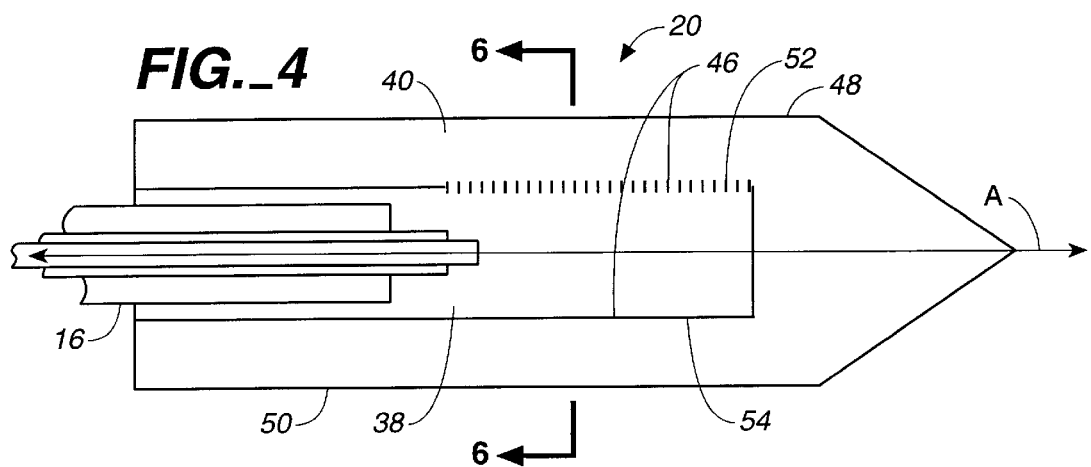
FIG._4
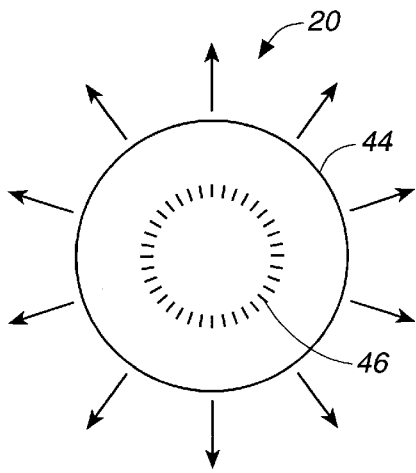
FIG._5
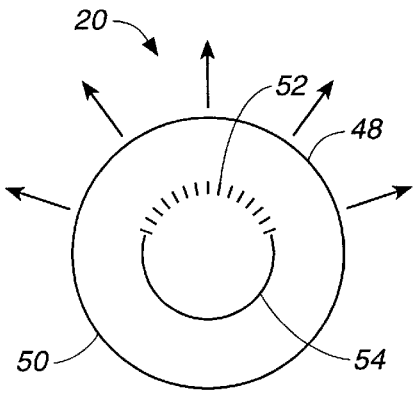
FIG._6

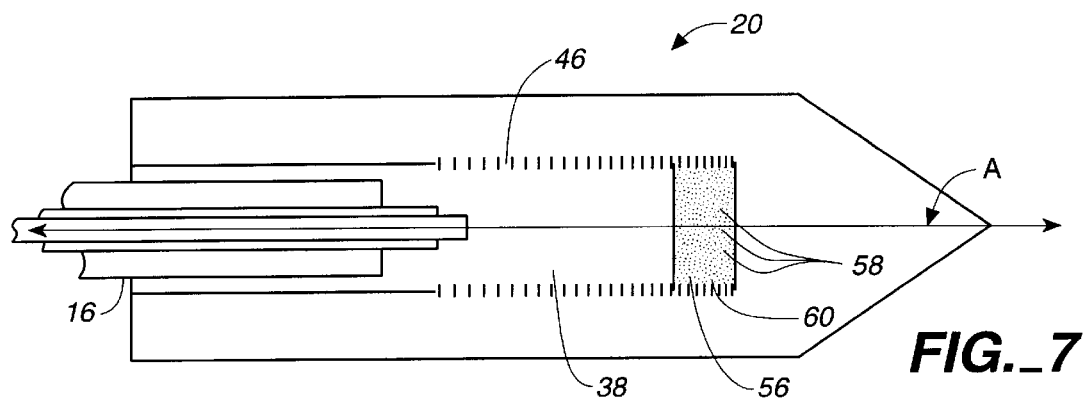
FIG._7
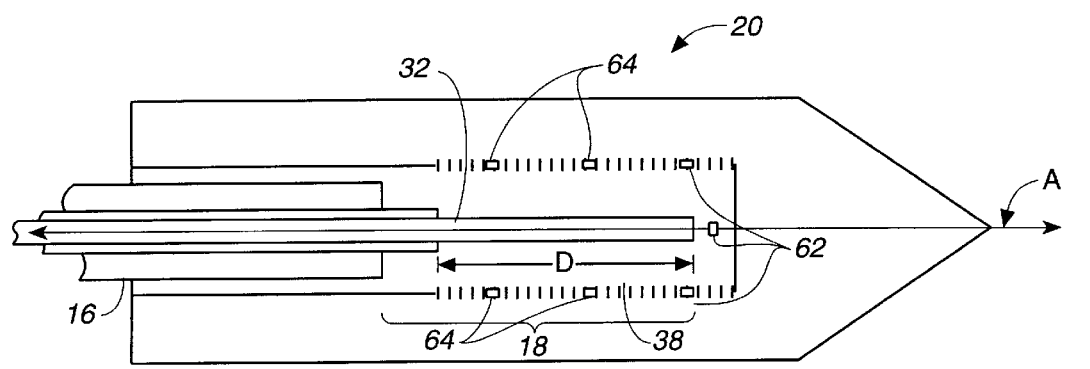
FIG._8
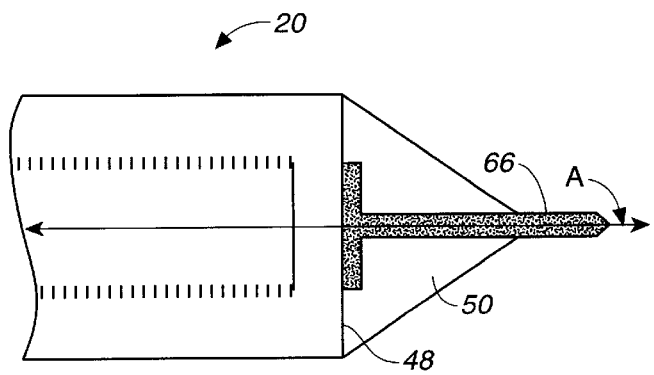
FIG._9

LIGHT-DIFFUSING DEVICE FOR AN OPTICAL FIBER, METHODS OF PRODUCING AND USING SAME, AND APPARATUS FOR DIFFUSING LIGHT FROM AN OPTICAL FIBER

This is a continuation of application Ser. No. 08/550,846, filed Oct. 31, 1995 now abandoned.

BACKGROUND OF THE INVENTION

This invention relates to a device used with an optical fiber to diffuse light from a light-emitting end of the optical fiber to an object to be illuminated, heated or irradiated thereby. More particularly, the present invention relates to a tip for an optical fiber which is useful for diffusing the light from the optical fiber in a radial distribution pattern relative to the axis of the tip and along a length of the tip.

There are several methods that have been developed to obtain a cylindrical distribution of light energy from an optical fiber. One such method involves choosing a ratio of the indices of refraction between the outer transparent cladding and the core of the optical fiber so that internal reflection within the core is substantially less than total. The fiber thus obtained is a radiator rather than an internally reflecting transmitter and thus, allows light to radiate outwardly from the core and through the transparent cladding. The fiber produced by this method, however, has failed to provide a uniform output intensity distribution which is desirable for a variety of applications, such as the processing of materials in which the materials must be irradiated uniformly.

Other methods that have been developed for obtaining a cylindrical distribution of light include texturing the outer surface of the core, such as by acid etching the core, to produce a ground glass effect, embedding light scattering particulates near the outer surface of the core or throughout the cladding, and combinations of these alterations of the optical fiber. However, these alterations often weaken the fiber, thereby limiting the usefulness of the fiber in a variety of applications, such as those requiring a flexible fiber which is resistant to breakage.

U.S. Pat. No. 5,296,777, issued on Dec. 14, 1993 to Doiron et al., discloses a tip for an optical fiber comprising a silicone core which abuts the core of the fiber, a surrounding layer of silicone with scatterers dispersed therein, and an outer cladding of plastic tubing. With this tip construction, when the light from the optical fiber meets the silicone core of the tip, the light is dispersed rather than guided within the silicone core, whereupon light dispersed towards and entering the scattering layer is further dispersed before exiting the outer cladding. The scattering layer is modified in terms of the arrangement and concentration of scatterers embedded therein to obtain a desired intensity distribution of the light diffused by the tip. However, as light is dispersed in the core as well as the scattering layer of the tip, modification of the scattering layer is an inadequate means of controlling the intensity distribution profile of the light diffused by the tip.

It is a primary object of the present invention to provide a light-diffusing tip for an optical fiber which provides light on the surface along the length of the tip useful for illuminating, heating or irradiating a targeted object.

It is another object of the present invention to provide a method of using such a light-diffusing tip, such as a method of inserting the light-diffusing tip into a targeted object and providing light on the surface and along a length of the tip sufficient to illuminate, to heat or to irradiate the targeted object.

Further objects of the present invention include providing an apparatus incorporating such a light-diffusing tip and providing a method of producing such a tip.

SUMMARY OF THE INVENTION

According to a primary aspect of the present invention, briefly and generally, an optical fiber is provided with a light-diffusing tip at a light-emitting end of the fiber. The light-diffusing tip has an inner light-transmissive material at its core which abuts the end of the optical fiber. The tip also has an outer light-transmissive material which circumferentially surrounds the core. The core material and the outer material are selected on the basis of their respective optical properties so that together they define a light guide for the light transmitted from the end of the fiber to the tip.

If the tip were merely a light guide, a light ray entering the tip would be confined within the core of the tip until it could exit the core at its distal end. However, in the present invention, the outer material of the tip is processed in such a way as to transmit light from the core of the light guide to the outer surface and along the length of the tip.

More particularly, the outer material is modified, for example, roughened or abraded, along its internal surface which is adjacent to the core material, such that light travelling along the light guide which encounters the modified surface is radially diffused toward the outside surface of the tip. Preferably, the internal surface of the outer material is modified in such a way that light travelling along the light guide is diffused to the outer surface of the tip in a substantially uniform intensity profile along the tip length.

In the present invention, the internal surface of the outer material may be uniformly abraded along the length of the tip. Alternately, the internal surface of the outer material may be increasingly abraded along the length of the tip toward its distal end. In a tip with an increasingly abraded internal surface, a light ray which remains guided within the core for some distance along the tip is likely to encounter, at some point further along the tip length, an abrasion on the internal surface that is sufficient to diffuse the light ray radially toward the outside surface of the tip. This minimizes the possibility of light rays being guided along the entire length of the tip to form an undesirable hot spot at the distal end of the tip.

Additional objects, advantages and features of the present invention will become apparent from the following description of its preferred embodiments, which description should be taken in conjunction with the accompanying drawings.

BRIEF DESCRIPTION OF THE DRAWINGS

FIG. 1 is an illustration of an apparatus for diffusing light from an optical fiber, according to the present invention;

FIG. 2 is an illustrative plot of light flux density relative to distance along a light-diffusing tip, according to the present invention;

FIG. 3 is a cross-sectional view of a light-diffusing tip, according to an embodiment of the present invention;

FIG. 4 is a cross-sectional view of a light-diffusing tip, according to another embodiment of the present invention;

FIG. 5 is a sectional view of the light-diffusing tip of FIG. 3, taken at section 5—5 thereof;

FIG. 6 is a sectional view of the light-diffusing tip of FIG. 4, taken at section 6—6 thereof;

FIG. 7 is a cross-sectional view of a light-diffusing tip, illustrating a possible combination of various features of the present invention;

FIG. 8 is a cross-sectional view of a light-diffusing tip, illustrating a possible combination of various features of the present invention;

FIG. 9 is a cross-sectional view of a distal end portion of a diffusing tip, illustrating a possible combination of various features of the present invention; and, FIG. 10 is a cross-sectional view of a portion of a diffusing tip, schematically illustrating a possible travel path of a light ray relative to the diffusing tip.

DESCRIPTION OF PREFERRED EMBODIMENTS

An apparatus 10 for diffusing light from an optical fiber according to the present invention is illustrated generally in FIG. 1. The apparatus includes a source of light energy 12, which is preferably a laser. The source 12 has a connection port 14 through which a proximal end 15 of an optical fiber 16 can be seated such that the source and the optical fiber are in optical communication.

The apparatus 10 may be configured to provide such optical communication between the source 12 and the optical fiber 16 in ways known in the art. Preferably, the apparatus is configured as disclosed in abandoned U.S. patent application Ser. No. 08/5551,009, entitled "Fiber Optic Radiation Transmission System, Connector System for an Optical Fiber, and Methods of Using Same" and filed concurrently herewith by Evans et al., the entire disclosure of which is incorporated by this reference.

When the apparatus 10 is in use, light energy is transmitted from the source 12 to the proximal end 15 of the optical fiber 16 via the optical communication configuration described above. The light energy travels the length (shown abbreviated) of the optical fiber 16 to a light-transmitting distal end 18.

According to the present invention, a diffusing tip 20 is provided to diffuse light that is emitted from the distal end 18 of the optical fiber 16 radially to an outside surface along a length of the tip. Light diffused in this manner can be usefully applied to an object 22, for example, to illuminate, to heat or to irradiate the object. While the object 22 is shown in cross-section as a solid material into which the diffusing tip 20 is inserted, it will be understood that the object may be any of a variety of objects in any of a variety of forms that might be usefully illuminated, heated or irradiated. By way of example, the object may be a heat sensitive material in annular form which is suitable for heat-shrinking around another annular structure upon the application of heat from the diffusing tip.

As further described herein, the diffusing tip 20 is designed to transmit light radially from its outside surface and along its length. The diffusing tip is particularly useful in applications in which it is desirable to illuminate, to heat, or to irradiate (hereinafter, to irradiate) an object uniformly, for example, in order to obtain uniform, predictable and reproducible results. Additionally, the diffusing tip 20 is well suited for applications in which, for safety reasons or to satisfy other processing requirements, it is necessary to irradiate the object uniformly. By way of example, it is often desirable to irradiate an object uniformly, particularly avoiding a non-uniform distribution of energy which can result in hot spots, or the undesirable concentration of light energy of high intensity in a localized area on the tip surface, and thus, a non-uniform and potentially damaging irradiation of the object.

FIG. 2 shows an illustrative plot of the light intensity, or flux density (in Watts/cm$^2$) of light, transmitted by a light-diffusing tip 20 relative to the distance along the length L of the tip, which is schematically depicted below the plot. Line 22 indicates the irradiating portion of the length of the tip, which may be of the same or different length than the length L of the tip. Preferably, the irradiating portion extends along the length L of the tip, as shown.

The bold-face line 24 shows a desirable uniform distribution of light energy transmitted radially from tip and along a length of the tip. The normal-face line 26 shows the light intensity profile for the diffusing tip 20, according to an embodiment further described herein. As shown in FIG. 2, the diffusing tip 20 provides a substantially uniform intensity profile of light energy radially transmitted at least along the irradiating portion 22 of the tip length L.

The light-diffusing tip 20 is shown in greater detail in FIG. 3, according to an embodiment of the present invention. The diffusing tip 20 extends for any of a variety of lengths, such as $L_1$ and $L_2$ described herein, along its longitudinal axis A and is coaxial with respect to the distal end 18 of the optical fiber 16. Hereinafter, the terms "proximal" and "distal" used in relation to the tip 20 refer to relative spatial locations of features nearest to and farthest from, respectively, the distal end 18 of the optical fiber 16.

As shown in FIG. 3, the diffusing tip 20 abuts and circumferentially surrounds the distal end 18 of the optical fiber 16. The optical fiber 16 may be a standard optical fiber, such as a graded-index fiber or a step-index fiber, having a core 32, typically composed of glass, a cladding 34, and a jacket 36. Preferably, the optical fiber is a step index fiber having a glass core. Preferably, the core 32 has an index of refraction from about 1.4 to 1.7. More preferably, the core 32 has an index of refraction of about 1.45.

At the distal end 18 of the optical fiber, the jacket 36 is preferably stripped away from the fiber to expose the core 32, as shown. The cladding 34 may be either stripped away from the distal end 18 of the fiber to expose the core 32, as shown, or flush with the distal end 18. In the latter case, the cladding 34 should be composed of a material which is resistant to operating temperatures.

The diffusing tip 20 is composed of a central core 38 and an outer covering 40 which abuts and circumferentially surrounds the central core. As shown, the central core 38 abuts and circumferentially surrounds the distal end 18 of the optical fiber 16. Thus, when light is emitted from the distal end 18, light rays are transmitted into the central core 38 of the diffusing tip.

The central core 38 and the outer covering, or sleeve 40, are composed of light-transmitting materials so that light transmitted into the core 38 can be transmitted to the outer surface 44 of the covering 40, as further described herein. These materials are selected to be resistant to operating temperatures, particularly operating temperatures ranging from about zero to about 250° C. Additionally, the core and the covering materials are selected to produce a light guide, wherein the inner surface 46 of the covering 40 confines the light rays to the core 38. More particularly, the materials of the core 38 and the covering 40 are selected based on their differing optical properties to define a light guide over the operating temperature range.

Thus, the diffusing tip 20 is basically a guiding device in which light is transmitted down the length of the core 38. However, the tip is modified in such a way (described below) that light is removed, or radially distributed, from the guiding device in a controlled manner along at least a portion of the length L of the tip. Light that is not removed is transmitted further down the guiding device where subsequently, it can be removed or further transmitted, as desired.

The guiding aspect of the tip 20 is generally achieved when the index of refraction of the core material 38 is greater than the index of refraction of the covering material 40. Thus, the core and covering materials are preferably selected such that at least along the irradiating portion 22 of the tip 20, the core material 38 has an index of refraction over the temperature range of interest that is greater than that of the covering material 40.

The guiding nature of the tip 20 may also be characterized by a quantity, the numerical aperture (N.A.), which is a measure of the light-gathering or collecting power of the tip. The numerical aperture is defined as follows:

$$N.A.=(n_1^2-n_2^2)^{1/2},$$

where $n_1$ is the index of refraction of the core material 38 and $n_2$ is the index of refraction of the covering material 40; and $$N.A.=\sin\theta,$$

where $\theta$ is the half angle of the acceptance cone (measured outside of the tip in air) for the tip, which is the maximum angle with respect to the longitudinal axis A of the tip 20 at which light rays can be accepted for transmission, or total internal reflection, down the core 38 of the tip. Thus, the core and the covering materials are preferably selected so that a tip having a very large numerical aperture may be obtained, if desired.

Preferably, the core material 38 has an index of refraction ranging from about 1.4 to about 1.8 and the covering material has an index of refraction ranging from about 1.3 to about 1.4 over the operating temperature range. More preferably, the core material 38 and the covering material 40 have indices of refraction of about 1.5 and 1.35, respectively, over the operating temperature range.

Most preferably, the core material 38 is an optically transparent silicone. The index of refraction for silicone is quite temperature sensitive, decreasing as the temperature increases.

The covering material 40 is preferably composed of a fluoropolymer, such as tetrafluoroethylene (TFE), fluorinated ethylene-propylene (FEP), or perfluoroalkoxy (PFA), and most preferably, composed of PFA. Such covering materials are commercially available from Zeus Industrial Products, Inc. of Orangeburg, S.C. The indices of refraction for fluoropolymers are generally not as temperature sensitive as the index of refraction for silicone.

Additionally, the covering 40 may be, and preferably is, impregnated with $BaSO_4$. $BaSO_4$ is useful for a number of purposes, for example, to enhance the smoothness of the light intensity profile of the diffusing tip, to enhance the stiffness of the tip (i.e., for tip insertion purposes), to provide a quiescent output coupling rate, and/or to provide radiopaque behavior (i.e., for visualization purposes). Preferably, the covering 40 is impregnated throughout with a uniform concentration of $BaSO_4$ particulates.

As mentioned above, while the tip 20 is basically a guiding device, it is modified so that light can be radially transmitted from the core 38 to the outer surface 44 of the tip and along at least a portion of the length L of the tip in a controlled manner. More particularly, the internal surface 46 of the covering 40 is modified in such a way as to remove a certain amount of the internally reflecting light from the core 38. The percentage of light removed from the core is a function of several factors, such as the operating temperature range and the relative indices of refraction of the core 38 and the cladding 40 over that temperature range, the angular distribution of the light transmitted from the optical fiber 16 into the tip 20, the angle of incidence of the light (described below), and the distribution of surface modifications on the internal surface 46.

By way of example, FIG. 10 schematically illustrates the travel of a light ray, represented by arrowed line 70, from the distal end of the optical fiber (not shown) through the diffusing tip 20. The light ray 70 travels within the central core 38 at an angle of incidence $\theta'$, which is measured relative to a line perpendicular to the internal surface 46 of outer covering 40. Upon meeting a relatively smooth portion 72 of the modified internal surface 46, the light ray may be internally reflected for further propagation within the core 38. Alternately, upon meeting a sufficient surface modification 74 of the modified internal surface 46, the light ray may be propagated into the outer covering 40, as represented by arrows 76, or further transmission from the tip 20. By way of example, the surface modification 74 may be of sufficient dimension or angular orientation to deflect the light ray from the core 38 and into the outer covering 40.

The internal surface 46 may be modified in a number of ways for this purpose, for example, roughened, textured, abraded, scratched, filed, rasped, scraped, notched, etched, purposefully flawed, or specially shaped, molded or otherwise formed into a non-homogeneous, edgy or angled surface 46, as depicted in FIG. 3. The modification of the internal surface 46 is such that, when a light ray that is transmitted down the core 38 encounters the internal surface 46, the modification alters the normal trajectory of the ray, allowing it to escape the core for transmission to the outer surface 44 of the diffusing tip.

Preferably, the tip 20 has an internal surface 46 that is modified sufficiently such that light is transmitted radially from the tip and along a length thereof in substantially uniform intensity distribution, as depicted in FIGS. 2 and 5. Particularly, light of substantially uniform intensity is transmitted radially, as depicted by the arrows (representing light rays) in FIG. 5, and along at least a portion of the length L of the tip, as shown in FIG. 2. Thus, light of substantially uniform intensity may be transmitted in a substantially cylindrical distribution pattern relative to the outside surface of the diffusing tip 20.

According to the present invention, the diffusing tip 20 may be adapted to transmit light in a preselected direction relative to the outer surface 44. For example, the preselected direction may be along the length L of the tip or azimuthal with respect to the longitudinal axis A of the tip. By way of illustration, the internal surface 44 of the covering 40 may be modified in such a way that light is transmitted radially from the tip, but on a side or along a portion 48 of the circumference of the tip to the exclusion of another side or circumferential portion 50 of the tip, as depicted in FIG. 6. FIG. 4 shows such a configuration in which the internal surface 46 is modified to be non-homogeneous only along a side or a portion 52 of the circumference, the remaining side or portion 54 being smooth or unmodified. Preferably, the surface modification is such that light of substantially uniform intensity is transmitted radially from portion 48 of the tip, as depicted by the arrows (representing light rays) in FIG. 6, and along at least a portion of the length L of the tip, as shown in FIG. 2.

The light-diffusing tip 20 may take a variety of forms and combinations of the various features described herein. For example, the tip 20 may include a scattering portion 56 at the distal end of the central core 38, as shown in FIG. 7. The scattering portion 56 is effective in preventing the formation of a hot spot at the distal end of the tip, in that it scatters light that has reached the distal end of the core 38 and thus, reduces the amount of light transmitted longitudinally further down the tip. The scattering portion 56 thus acts as collector of photons.

The scattering portion 56 may be much shorter in length than the irradiating portion 22 of the tip 20. For example, for a tip that is two centimeters in length, the scattering portion may be two millimeters in length. Scattering portion 56 is composed of a suitable scattering material for scattering light in the manner described above, and may include particulates 58 dispersed in a relatively homogeneous medium 60.

Preferably, scattering portion 56 is composed of an optically clear scattering material which is optically and chemically inert at operating temperatures. For example, the scattering material may be selected from the group consisting aluminum oxide, titanium dioxide and diamond powder. The scattering material is preferably aluminum oxide, and more preferably, includes aluminum oxide particulates. Most preferably, the scattering material includes a silicone medium with aluminum oxide particulates uniformly dispersed therein.

As described herein, the diffusing tip 20 has an internal surface 46 which is modified such that light is radially transmitted from the core 38 in a controlled manner. In FIGS. 3–6, 8 and 9, the modified internal surface 46 is depicted as being relatively constant in terms of the distribution of surface modifications adjacent to and along a length of the core 38. This relatively constant distribution of surface modifications along the internal surface 46 may be obtained, for example, by uniformly abrading the internal surface from a proximal portion to a distal portion thereof.

The internal surface 46 may be modified in a more differentiated manner, if desired. By way of example, the internal surface 46 of the covering 40 may be modified such that the distribution of surface modifications increases along a length of and towards the distal end of the internal surface, as depicted in FIG. 7. This distribution may be obtained, for example, by increasingly abrading the internal surface from a proximal portion to a distal portion thereof. Such a distribution allows an amount of light to be transmitted radially from the core 38 via its proximal, less modified portions of the internal surface 46, while allowing a sufficient amount of light to be transmitted further down the core 38 to be transmitted radially from the core at a distal location, via its distal, more modified portions of the internal surface. Thus, the tip 20 diffuses light controllably, in a desired light intensity profile, radially and along an irradiating portion 22 of its length L.

The above-described distribution of surface modifications is shown as an increasing spatial distribution in FIG. 7, wherein the spatial distribution is more concentrated towards the distal end of the internal surface 46. By way of example, the surface modifications may be increasingly concentrated in a graduated manner, such that at locations corresponding to 10, 20, and up to 100 percent of the irradiating portion 22 of the tip length, the light output couplings are 10, 20, and up to 100 percent of the light travelling down the irradiating portion, respectively. Alternately or additively, the distribution of surface modifications may be an increasing dimensional distribution, wherein the size of the surface modifications increases along a length of and towards the distal end of the internal surface.

The surface modifications of the diffusing tip 20 are useful to control the light intensity profile at the outer surface 44 of the tip. By way of example, the flux density, or light intensity, profile 26 for a diffusing tip 20 relative to the length L from the proximal to the distal end of the tip is shown in FIG. 2. The profile is for a diffusing tip 20 having a central core 38 of silicone, a covering 40 of PFA impregnated with $BaSO_4$ and uniformly abraded along internal surface 46, a scattering portion 56 of about 2 mm along tip length L of a silicone medium 60 in which aluminum oxide particulates 58 are uniformly dispersed, and a length L of one centimeter. Also shown is a desirable uniform flux density, or light intensity, profile 24 for a diffusing tip.

The light intensity profile 26 substantially follows the desired profile 24 in its rise to a first peak 28. The first peak 28 reflects the light output coupling resulting from the surface modifications along the internal surface 46 of the covering 40 at a proximal end of the irradiation portion 22. The profile 26 dips only slightly relative to the desired profile 24 before returning to meet the desired profile 24 in its rise to a second peak 30. (This dip may result from one or more of the factors described herein as possibly affecting the percentage of light removed from the core 38 of the diffusing tip 20.) The second peak 30 reflects the light output coupling resulting from the surface modifications along the internal surface 46 of the covering 40 at a distal end of the irradiation portion 22. Finally, the profile falls off in substantial conformity with the desired profile 24 towards the end of the irradiating portion 22 of the tip. Thus, the light intensity profile 26 for the diffusing tip 20 substantially follows the desired uniform light intensity profile 24, providing a substantially uniform light intensity profile along the irradiating portion 22 of the tip length. The diffusing tip 20 thus eliminates or reduces hot spot formation on its irradiating outer surface.

The diffusing tip 20 may include a temperature sensor to measure temperature at various tip locations, for example, to monitor for hot spot formation. FIG. 8 illustrates several temperature sensors, such as individual temperature sensors 62 and annular, or o-ring, temperature sensors 64, located, by way of example, adjacent to and along the internal surface 44 of the core 38 and within the core 38 towards its distal end. The temperature sensors are preferably optical temperature sensors. Most preferably the optical temperature sensors are composed of alexandrite, which has temperature-dependent fluorescing properties. These fluorescing properties can be detected in ways known in the art, for example, by a phase-sensitive detection system, and related to the temperature of the tip 20 at a particular location.

According to an aspect of the invention, the lateral stability or the strength of the light-diffusing tip 20 may be enhanced, as shown in FIG. 8. This aspect of the invention is preferred when the diffusing tip is relatively long, such as two centimeters in length, or when the tip is inserted into, or is used to penetrate or to puncture, a target object 22. According to this aspect of the invention, the core 32 of the optical fiber 16 extends longitudinally into the central core 38 of the tip 20 for a distance D sufficient to provide the desired stability or strength. Additionally, the central core 38 and the core 32 are selected such that along the distance D, when light is transmitted from the distal end 18 of the optical fiber 16, the light is transmissible from the core 32 to the central core 38 over the operating temperature range.

Thus, according to this aspect of the invention, the central core 38 has an index of refraction over the operating temperature range which is equal to or greater than that of the core 32. Preferably, the central core 38 has an index of refraction over the operating temperature range which matches that of the core 32. Alternately, for example, when available materials are limited, the central core 38 may have an index of refraction over the operating temperature range which is greater than that of the core 32, so that light is transmissible from the core 32 to the central core 38 over the operating temperature range. As described above, the core 32 of the optical fiber 16 is typically made of glass and the central core 38 is preferably made of silicone. The glass core 32 has an index of refraction which is not as temperature sensitive as that of silicone. The index of refraction for the core 32 is typically from about 1.4 to about 1.7, and preferably, about 1.45, while the index of refraction for the central core 38 is typically from about 1.4 to 1.8, and preferably, about 1.5.

The diffusing tip 20 may terminate in a variety of ways to suit various applications. By way of example, the diffusing tip may terminate in a blunt distal end, as indicated by the broken line 48 of FIG. 3, thus having a length $L_1$. Alternately, the tip may terminate in a tapered or pointed distal end, as indicated by distal end 50, thus having a length $L_2$. In the latter example, the distal end 50 may be an independent structure which is attached to the diffusing tip 20, for example, at broken line 48, or may be formed as part of the covering 40.

Additionally, the tip may terminate in a distal end, such as 48 or 50, which is adapted to facilitate insertion of the tip into, or the puncturing or penetration of, the object 22 to be irradiated. For example, the distal end of the tip may be sharp, pointed, and/or have a puncturing tip 66 attached to or molded into the tip structure, as illustrated in FIG. 9. The puncturing tip 66 is composed of a material sturdy enough for efficient and safe puncturing, such as ceramic or gold. Preferably, the puncturing tip 66 is composed of a sturdy material of high reflectivity, such as 24 karat gold, so that light is not absorbed by the material to produce a hot tip.

The diffusing tip 20 can be produced in a variety of lengths, some of which may be better suited for a particular application depending, for example, on the geometry of the object 22 to be irradiated. According to two particular embodiments of the invention, the diffusing tip is produced in lengths of one centimeter and two centimeters, respectively.

A method of producing a diffusing tip 20 according the invention is now described. A light-transmissive annular covering or tip material 40 is provided. The tip material 40 is either provided with a closed distal end or the end is processed, such as by molding or heat treatment, to close the distal end. Optionally, a point may be formed at the distal end of the tip 40 using a tipping die, a long needle-shaped mandrel, and heat treatment.

The internal surface 46 of the closed tip 40 is modified, as described above. A brush, preferably made of wire, is inserted into the open, proximal end of the tip 40 and rotated therein, preferably uni-directionally, so that the bristles of the brush abrade the internal surface 46 of the tip. For a uniformly abraded surface, the wire brush is rotated uniformly as it is pulled outwardly from the distal to the proximal end of the tip, for example, by rotating the brush a certain number of turns as it is pulled outwardly a given distance. For an increasingly abraded surface, the wire brush is rotated more, initially, and less, as it is pulled outwardly towards the proximal end of the tip. Alternately, the internal surface 40 may be modified using a grinding tool to abrade the surface. Preferably, the grinding tool is impregnated with diamond powder which has good abrasive properties and is optically inert.

The modified tip 40 is filled with a light-transmissive core material 38, which is provided as a fluid. The distal end 18 of an optical fiber 16, which may be stripped to expose a portion, or an extended portion (as in FIG. 8), of its core 32, is placed in the modified tip 40. Once the modified tip 40 is filled and the optical fiber 16 is placed therein, the tip is heat treated sufficiently to solidify, or to cure, the core material 38 and thus, produce the diffusing tip 20. Alternately, a temperature sensor may be placed in the tip 20 prior to heat treating, so that it becomes set with respect to the cured core material 38.

The method of producing the diffusing tip 20 may include filling the distal end of the modified tip 40 with a light-transmissive material 60 having a scattering material 58 dispersed therein, before filling the remaining proximal portion of the modified tip 40 with the light-transmissive core material 38. Further, the method may include heat treating the modified tip 40 sufficiently to solidify, or to cure, the material 60, for example, to form the scattering portion 56 of FIG. 7, prior to filling the remaining proximal portion of the modified tip and placing the distal end of the optical fiber therein, and subsequently, heat treating the modified tip to form the diffusing tip 20.

The diffusing tip 20 can be used in a variety of ways, such as to illuminate, to heat or to irradiate an object, or a selected material, with light from a light-emitting portion 22 of the outside surface 44 of the tip. The tip may be used to transmit light to the material in a substantially uniform intensity profile along the length of the light-emitting portion 22. This aspect of the invention may be particularly useful for certain applications, such as the heating or photon-irradiation of a volumetric material or the illumination of an annular material, where uniform irradiation is desirable. Additionally, this aspect of the invention is often preferred, particularly when the selected material is bodily tissue which may be undesirably damaged by non-uniform irradiation, such as irradiation having an irradiation profile along the length of the tip which includes intense hot spots.

Thus, the diffusing tip 20 of the present invention is particularly useful in the treatment of bodily tissue. In such applications, the diffusing tip can be used intraluminally or interstitially to irradiate bodily tissue, such as tissue that is normal or abnormal, or affected with benign or malignant tumors or cancers. When used intraluminally, the diffusing tip is simply extended into the lumen of the bodily tissue. When used interstitially, the tip is inserted into the tissue, such as by puncturing or otherwise penetrating the tissue, and the tissue is then irradiated.

In a particularly preferred application of the diffusing tip 20, the bodily tissue to be irradiated is prostatic. The tip is inserted into a lobe of the prostate and the tissue is irradiated sufficiently to necrose a volume of the tissue. The tissue is preferably irradiated with light of a substantially uniform intensity profile along the irradiating portion of the tip to avoid charring the tissue, for example, by undesirable hot spot irradiation. The tip is most preferably used in this manner to irradiate prostatic tissue that is affected by benign prostatic hypertrophy. Irradiation of prostatic tissue affected by benign prostatic hypertrophy can be accomplished using an apparatus and a method, such as the apparatus and method of U.S. patent application Ser. No. 07/681,225 of Conn et al., filed on Apr. 5, 1991, and U.S. patent application Ser. No. 07/941,481 of Conn et al., filed on Sep. 8, 1992, both now abandoned the entire disclosures of which are incorporated herein by this reference.

Although the various aspects of the present invention have been described with respect to the preferred embodiments thereof, it will be understood that the invention is entitled to protection within the full scope of the appended claims.

It is claimed:

1. A device for diffusing light supplied thereto by an optical fiber, comprising:

an optical fiber having a light-transmitting end;

a light-transmissive first material abutting and circumferentially surrounding the end of said optical fiber; and a light-transmissive second material abutting and circumferentially surrounding said first material, said first and second materials defining a light guide when light is transmitted from the end of the optical fiber to the first material, said second material having an internal surface modified sufficiently to transmit light travelling along the light guide to an outside surface along a length of said second material.

2. The device of claim 1 wherein along a length of said first material, said first material has an index of refraction that is greater than that of said second material.

3. The device of claim 2 wherein said first material has an index of refraction from about 1.4 to about 1.8.

4. The device of claim 2 wherein said second material has an index of refraction from about 1.3 to about 1.4.

5. The device of claim 2 wherein said first material is silicone.

6. The device of claim 2 wherein said second material is a fluoropolymer.

7. The device of claim 2 wherein said second material is impregnated with $BaSO_4$.

8. The device of claim 1 wherein the internal surface of said second material is abraded.

9. The device of claim 8 wherein the internal surface of said second material is increasingly abraded along a length thereof towards a distal end thereof.

10. The device of claim 1 wherein light is transmitted in a preselected direction relative to the outside surface of said second material.

11. The device of claim 10 wherein the preselected direction is azimuthal with respect to the outside surface of said second material.

12. The device of claim 10 wherein the preselected direction is along a length of the outside surface of said second material.

13. The device of claim 1 wherein light is transmitted in a substantially uniform intensity profile along a length of the outside surface of said second material.

14. The device of claim 1 wherein said second material forms a tip at a distal end thereof, said tip facilitating placement of the second material into a material selected for receiving light therefrom.

15. The device of claim 1 further comprising a tip attached to said second material at a distal end thereof, said tip facilitating placement of the second material into a material selected for receiving light therefrom.

16. The device of claim 14 or 15 wherein said tip is adapted for puncturing the selected material.

17. The device of claim 1 wherein an exposed core of said optical fiber extends a distance into said first material and said first material and the core are selected such that when light is transmitted from the end of the optical fiber to the first material, light is transmissible from the core to the first material along that distance.

18. The device of claim 17 wherein said first material has an index of refraction that is equal to or greater than that of the core along the distance.

19. The device of claim 18 wherein said first material has an index of refraction from about 1.4 to 1.8.

20. The device of claim 18 wherein the core has an index of refraction from about 1.4 to about 1.7.

21. The device of claim 18 wherein said first material is silicone.

22. The device of claim 18 wherein the core is glass.

23. The device of claim 1 wherein said first material has a light scatterer disposed in a distal end portion thereof.

24. The device of claim 23 wherein the light scatterer is selected from a group consisting of aluminum oxide, titanium dioxide and diamond powder.

25. The device of claim 1 wherein said first material has a temperature sensor disposed in a distal end portion thereof.

26. The device of claim 1 wherein said first material has a temperature sensor disposed along a length thereof adjacent to the internal surface of said second material.

27. The device of claim 25 or 26 wherein the temperature sensor is an optical temperature sensor.

28. An apparatus for diffusing light from an optical fiber, comprising:

a source of light energy;

an optical fiber having a proximal end, optically coupled to said source, and a light-transmitting distal end, said optical fiber carrying light energy from the proximal end to the distal end;

a light-transmissive first material abutting and circumferentially surrounding the distal end of said optical fiber; and a light-transmissive second material abutting and circumferentially surrounding said first material, said first and second materials defining a light guide when light is transmitted from the proximal end of the optical fiber to the first material, said second material having an internal surface modified sufficiently to transmit light travelling along the light guide to an outside surface along a length of said second material.

29. The apparatus of claim 28 wherein the internal surface of said second material is abraded.

30. The apparatus of claim 29 wherein the internal surface of said second material is increasingly abraded along a length thereof towards a distal end thereof.

31. The apparatus of claim 28 wherein light is transmitted in a preselected direction relative to the outside surface of said second material.

32. The apparatus of claim 28 wherein light is transmitted in a substantially uniform intensity profile along a length of the outside surface of said second material.

33. The apparatus of claim 28 further comprising a tip at a distal end of said second material, said tip adapted for puncturing a material into which the second material is to be inserted.

34. The apparatus of claim 28 wherein an exposed core of said optical fiber extends a distance into said first material and said first material and the core are selected such that when light is transmitted from the distal end of the optical fiber to the first material, the light is transmissible from the core to the first material along that distance.

35. The apparatus of claim 28 wherein said source of light energy is a laser.

36. A method of producing a light-diffusing tip for an optical fiber, comprising:

(a) providing an optical fiber having a light-transmitting end;

(b) providing a first light-transmissive material as a fluid which solidifies upon sufficient heat treatment;

(c) providing a tip of a second light-transmissive material, the first and second materials defining a light guide when the first material abuts and circumferentially surrounds the end of the optical fiber, the second material abuts and circumferentially surrounds the first material, and light is transmitted from the end of the optical fiber to the first material;

(d) modifying an internal surface of the tip;

(e) after (d), filling the tip with the first material;

(f) after (d), placing the end of the optical fiber in the tip;

(g) after (e) and (f), heat treating the tip sufficiently to solidify the first material.

37. The method of claim 36 wherein said tip providing includes providing a tip with a pointed end.

38. The method of claim 37 wherein said tip providing includes molding the tip to form the pointed end.

39. The method of claim 36 wherein said modifying of the internal surface includes abrading the internal surface.

40. The method of claim 39 wherein the abrading includes increasingly abrading the internal surface of the tip from a proximal end to a distal end thereof.

41. The method of claim 39 wherein the abrading includes rotating a brush within the tip such that bristles of the brush abrade the internal surface.

42. The method of claim 39 wherein the abrading includes rotating a drill bit within the tip such that the bit abrades the internal surface.

43. The method of claim 36 wherein the first material is silicone.

44. The method of claim 36 wherein the second material is a fluoropolymer.

45. The method of claim 36 wherein said providing of the optical fiber includes exposing the core at the end of the optical fiber, the first material and the core selected such that when the first material abuts and circumferentially surrounds the core and light is transmitted from the end of the optical fiber to the first material, light is transmissible from the core to the first material.

46. The method of claim 45 wherein the first material is silicone and the core is glass.

47. The method of claim 36 wherein the first material includes a first portion, which has a light-scattering material dispersed therein, and a second portion, wherein the second portion and the second material define the light guide when the second portion is circumferentially surrounded by the second material, and wherein said filling of the tip includes filling a distal end portion of the tip with the first portion prior to filling a remaining portion of the tip with the second portion.

48. The method of claim 47 further comprising heat treating the tip sufficiently to solidify the first portion prior to said placing of the end of the optical fiber.

49. The method of claim 47 wherein the first and second portions are silicone and the scattering material is selected from a group consisting of aluminum oxide, titanium dioxide and diamond powder.

50. The method of claim 36 further comprising placing a temperature sensor in the tip prior to said heat treating of the tip.

51. The method of claim 36 wherein said providing of the tip includes providing a pointed portion at a distal end thereof.

52. The method of claim 36 wherein said providing of the tip includes providing a puncturing device at a distal end thereof.

53. A method of delivering light energy to a selected material, comprising:

providing a source of light energy;

providing an optical fiber having a proximal end, optically coupled to said source, and a light-transmitting distal end, the optical fiber carrying light energy from the proximal end to the distal end;

providing a tip comprising an inner portion which abuts the distal end of the optical fiber and circumferentially surrounds at least a portion of the optical fiber, and an outer portion which abuts and circumferentially surrounds the inner portion, the inner and outer portions being of a light-transmissive first material and a light-transmissive second material, respectively, which define a light guide when light is transmitted from the distal end of the optical fiber to the inner portion, the outer portion having an internal surface modified sufficiently to transmit light travelling along the light guide to a light-emitting portion of an outside surface along a length of the outer portion; and irradiating a selected material with light from the light-emitting portion of the tip.

54. The method of claim 53 wherein the light-emitting portion transmits light in a substantially uniform intensity profile along a length thereof.

55. The method of claim 54 wherein the selected material is annular and said irradiating illuminates an annulus thereof.

56. The method of claim 54 wherein the selected material is volumetric and said irradiating heats a volume thereof.

57. The method of claim 54 wherein the selected material is volumetric and said irradiating irradiates a volume thereof with photons.

58. The method of claim 54 wherein the selected material is bodily tissue.

59. The method of claim 58 further comprising inserting the tip into the tissue, wherein said irradiating includes irradiating the tissue sufficiently to necrose a volume thereof.

60. The method of claim 58 wherein the tissue is tumorous.

61. The method of claim 58 wherein the tissue is prostatic.

62. The method of claim 61 wherein the tissue is affected by benign prostatic hypertrophy.

63. The method of claim 62 further comprising inserting the tip into a lobe of a prostate, wherein said irradiating includes irradiating the tissue sufficiently to necrose a volume thereof.

64. A device for diffusing light supplied thereto by an optical fiber, comprising:

an optical fiber having a light-transmitting end;

a light-transmissive first material abutting and circumferentially surrounding the end of said optical fiber, said first material having a temperature sensor disposed in a distal end portion thereof; and a light-transmissive second material abutting and circumferentially surrounding said first material, said first and second materials defining a light guide when light is transmitted from the end of the optical fiber to the first material, said second material having an internal surface modified sufficiently to transmit light travelling along the light guide to an outside surface along a length of said second material.

65. A device for diffusing light supplied thereto by an optical fiber, comprising:

an optical fiber having a light-transmitting end;

a light-transmissive first material abutting and circumferentially surrounding the end of said optical fiber; and a light-transmissive second material abutting and circumferentially surrounding said first material, said first and second materials defining a light guide when light is transmitted from the end of the optical fiber to the first material, said second material having an internal surface modified sufficiently to transmit light travelling along the light guide to an outside surface along a length of said second material, and said first material having a temperature sensor disposed along a length thereof adjacent to the internal surface of said second material.

66. The device of claim 64 or 65 wherein the temperature sensor is an optical temperature sensor.

67. A method of producing a light-diffusing tip for an optical fiber, comprising:

(a) providing an optical fiber having a light-transmitting end;

(b) providing a first light-transmissive material as a fluid which solidifies upon sufficient heat treatment;

(c) providing a tip of a second light-transmissive material, the first and second materials defining a light guide when the first material abuts and circumferentially surrounds the end of the optical fiber, the second material abuts and circumferentially surrounds the first material, and light is transmitted from the end of the optical fiber to the first material;

(d) modifying an internal surface of the tip;

(e) placing a temperature sensor in the tip;

(f) after (d), filling the tip with the first material;

(g) after (d), placing the end of the optical fiber in the tip; and (h) after (f) and (g), heat treating the tip sufficiently to solidify the first material.

* * * * *